US011404169B2

(12) United States Patent
Mbanefo et al.

(10) Patent No.: US 11,404,169 B2
(45) Date of Patent: Aug. 2, 2022

(54) COLLABORATION TOOL FOR HEALTHCARE PROVIDERS

(71) Applicant: Accenture Global Services Limited, Dublin (IE)

(72) Inventors: Primrose Mbanefo, Newmarket (GB); Gregory L. Smith, Mesa, AZ (US)

(73) Assignee: Accenture Global Services Limited, Dublin (IE)

( * ) Notice: Subject to any disclaimer, the term of this patent is extended or adjusted under 35 U.S.C. 154(b) by 1013 days.

(21) Appl. No.: 15/164,348

(22) Filed: May 25, 2016

(65) Prior Publication Data
US 2017/0004273 A1    Jan. 5, 2017

Related U.S. Application Data

(60) Provisional application No. 62/186,485, filed on Jun. 30, 2015.

(51) Int. Cl.
*G16H 80/00* (2018.01)

(52) U.S. Cl.
CPC .................. *G16H 80/00* (2018.01)

(58) Field of Classification Search
USPC ........................................ 705/2, 3
See application file for complete search history.

(56) References Cited

U.S. PATENT DOCUMENTS

| | | | | |
|---|---|---|---|---|
| 7,774,132 B2* | 8/2010 | DeGrazia | ............... | G01C 21/20 340/988 |
| 2003/0033079 A1* | 2/2003 | Endicott | ................ | G01C 21/20 701/431 |
| 2005/0201362 A1* | 9/2005 | Klein | ................ | H04M 3/42263 370/352 |
| 2008/0132252 A1* | 6/2008 | Altman | .............. | G06Q 30/0207 455/457 |
| 2008/0256192 A1* | 10/2008 | Pinard | .................... | G06Q 30/02 709/206 |
| 2010/0198614 A1* | 8/2010 | Chopra | .................. | G16H 40/20 705/2 |
| 2011/0060996 A1* | 3/2011 | Alberth, Jr. | ............. | H04L 51/24 715/736 |
| 2013/0325499 A1* | 12/2013 | Kohane | .......... | G06Q 10/063114 705/2 |

(Continued)

OTHER PUBLICATIONS

Vineet Arora et al., "A Model for Building a Standardized Hand-off Protocol," http://uthscsa.edu/gme/documents/Competencies/Sleep,%20Fatigue,%20Duty%20hours/Patient%20Handoff%20Reference.pdf, Nov. 2006, 10 pages.

*Primary Examiner* — Joshua B Blanchette
(74) *Attorney, Agent, or Firm* — Harrity & Harrity, LLP

(57) ABSTRACT

A device may communicate with a first device to receive first data. The device may communicate with a second device to receive second data. The device may combine the first data and the second data into a user interface. The user interface may provide a single location for displaying communications with the set of entities and with a system associated with the set of entities. The user interface may include a first section that provides information that is persistently presented in the user interface. The user interface may include a second section that provides information that is selectively presented in the user interface. The device may provide the user interface for display.

20 Claims, 14 Drawing Sheets

(56) References Cited

U.S. PATENT DOCUMENTS

| | | | |
|---|---|---|---|
| 2014/0095631 A1* | 4/2014 | Ravi | G06Q 10/107 709/206 |
| 2014/0195272 A1* | 7/2014 | Sadiq | G06Q 40/08 705/4 |
| 2014/0278550 A1* | 9/2014 | Pestka | G06F 19/00 705/3 |

* cited by examiner

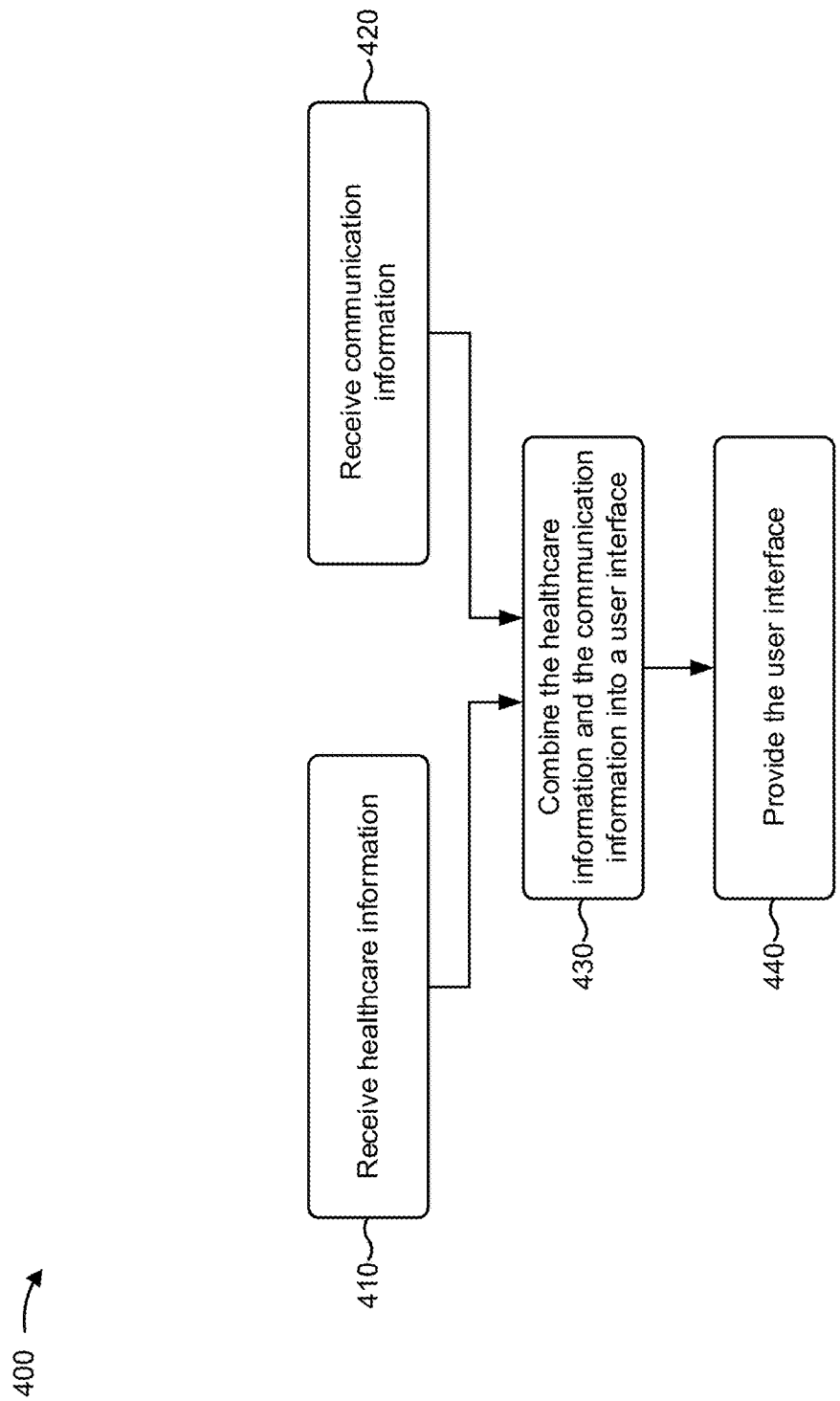

COLLABORATION TOOL FOR HEALTHCARE PROVIDERS

RELATED APPLICATION

This application claims priority under 35 U.S.C. § 119 to U.S. Provisional Patent Application No. 62/186,485, filed on Jun. 30, 2015, the content of which is incorporated by reference herein in its entirety.

BACKGROUND

In a healthcare environment, such as a hospital, healthcare providers may utilize a number of different devices to communicate with each other or with family members of patients. Such devices may include tablet computers, mobile phones, pagers, laptop computers, desktop computers, or the like. These devices may exchange data representing information about a patient, availability of a provider, location of a resource, a task to be performed, or the like. However, excessive communications being provided by different devices may cause distractions and/or result in interruptions to hospital services.

SUMMARY

According to some possible implementations, a device may include one or more processors. The one or more processors may communicate with a first device to receive first data. The first data may be associated with a set of entities. The one or more processors may communicate with a second device to receive second data. The second data may be associated with a set of communication sources and a set of communication mediums utilized by the set of entities and a user of the device. The one or more processors may combine the first data and the second data into a user interface. The user interface may provide a single location for displaying communications with the set of entities and with a system associated with the set of entities. The user interface may include a first section that provides information that is persistently presented in the user interface. The user interface may include a second section that provides information that is selectively presented in the user interface. The one or more processors may provide the user interface for display.

According to some possible implementations, a non-transitory computer-readable medium may store one or more instructions that, when executed by one or more processors, may cause the one or more processors to receive, from a healthcare provider system, healthcare information associated with a set of healthcare providers. The one or more instructions, when executed by one or more processors, may cause the one or more processors to receive communication information associated with the set of healthcare providers and a user of the device. The one or more instructions, when executed by one or more processors, may cause the one or more processors to combine the healthcare information and the communication information into a user interface. The user interface may include a first section that provides information that is persistently presented in the user interface and relates to a set of alerts or a set of tasks associated with a set of patients of the set of healthcare providers and the user. The user interface may include a second section that selectively provides positive reinforcement to the user based on utilization of the user interface. The one or more instructions, when executed by one or more processors, may cause the one or more processors to provide the user interface for display. The one or more instructions, when executed by one or more processors, may cause the one or more processors to update the second section of the user interface based detecting utilization of the user interface by the user.

According to some possible implementations, a method may include receiving, by one or more devices and from a set of healthcare provider systems, healthcare information associated with a set of healthcare providers. The method may include receiving, by the one or more devices, communication information associated with a set of communication sources and a set of communication mediums utilized by the set of healthcare providers and a user of a user device. The method may include combining, by the one or more devices, the healthcare information and the communication information into a user interface. The user interface may provide a single location for the user to manage communications with the set of healthcare providers and with the set of healthcare provider systems. The user interface may include a first section that provides information that is persistently presented in the user interface. The user interface may include a second section that provides positive reinforcement to the user based on utilization of the user interface. The method may include providing, by the one or more devices, the user interface for display.

BRIEF DESCRIPTION OF THE DRAWINGS

FIG. 4 is a flow chart of an example process for providing a healthcare management and communications user interface.

DETAILED DESCRIPTION

Figure 1:
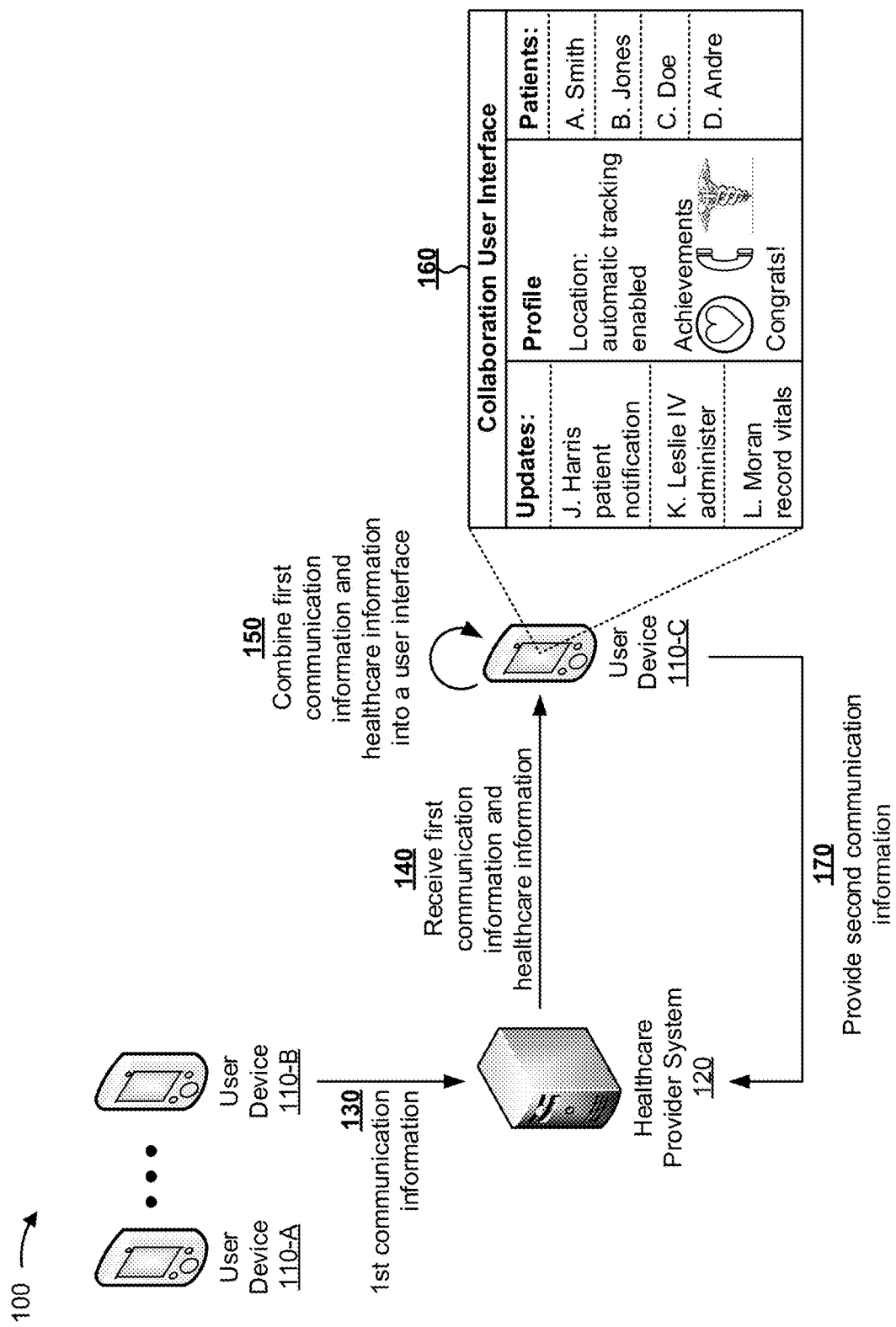
FIG. 1 is a diagram of an overview of an example implementation described herein.

The following detailed description of example implementations refers to the accompanying drawings. The same reference numbers in different drawings may identify the same or similar elements.

Healthcare providers, such as nurses, doctors, nurse aids, hospital support staff, or the like, utilize multiple devices to communicate with each other and with healthcare provider systems (e.g., electronic medical record (EMR) systems, computerized physician order entry (CPOE) systems, or scheduling systems). For example, a nurse in a hospital may utilize a tablet computer to access EMR systems, CPOE systems, or the like, a pager device so that the nurse may be reached by hospital personnel, a smart phone to access calendar services, or the like. Unfortunately, managing multiple devices and healthcare provider systems is difficult, time consuming, and creates interruptions for the healthcare providers. These communication challenges prevent healthcare providers from efficiently performing their duties and caring for patients.

For example, communication challenges within hospitals, and across multiple departments and multiple shifts, may occur due to interruptions, patient transitions between hospital units, communication between nurses and patients and/or patient families, communication between nurses and physicians, or the like. Interruptions are to be expected in healthcare services, and sometimes provide critical information to a healthcare provider. However, the sheer frequency at which interruptions currently occur in hospitals poses challenges. For example, a nurse's pager or mobile phone may receive messages or calls every few minutes, and not all of the information provided to the nurse is urgent or critical. Furthermore, the non-critical information may disrupt critical processes like drug administration.

Patient transitions between units are continuous in a hospital setting. During some patient transitions, both a sending nurse and a receiving nurse meet to exchange a summary of pertinent patient information. Thus, the sending nurse may need to identify and locate the receiving nurse, and the receiving nurse needs to be available for the patient transition. During some patient transitions, it may not be necessary for the two nurses to physically meet. For example, if both nurses are currently available, a video call could replace the face-to-face discussion. If the receiving nurse is not immediately available, text, audio, and/or video messages with the patient transition information may be provided to the receiving nurse for later review. Without a standardized way of transferring the patient transition information, there is also the potential for confusion during any patient transition.

Communication between nurses and patients/families may be critical to healthcare delivery, but may detract from patient care. For example, assume that a patient in an intensive care unit (ICU) of a hospital has ten different family members call the hospital within three hours to get an update on the patient's condition. Such frequent communication is normal family behavior, but may interrupt and detract from the patient's care.

Communications between physicians and nurses present multiple challenges for both the physicians and the nurses. For example, a physician may need to identify which nurse is caring for the physician's patient, a nurse may need to identify which physician to contact for a patient, a physical location of a healthcare provider may need to be determined, or the like. In one example, a nurse may page a physician, but the physician's return call to the nurse may be put on hold because the nurse has become unavailable. Furthermore, when the physician's return call is not answered, both the nurse and the physician may have to remember what the initial page was regarding. A healthcare provider may not know which communication device (e.g., a pager, a smart phone, a tablet, a hospital tracking system, or the like) or which communication medium (e.g., a voice call, a video call, a text message, an email message, or the like) to use to contact another healthcare provider. Thus, the healthcare provider may utilize all communication devices and/or communication mediums to try to contact the other healthcare provider, which creates a lot of interruptions for both healthcare providers.

Implementations, described herein, may provide a collaboration tool for healthcare providers that minimizes or eliminates communication challenges associated with interruptions, patient transitions between hospital units, communication with patients and/or patient families, communication between healthcare providers, or the like. The collaboration tool may include an application for a mobile computation and communication device. The collaboration tool may integrate multiple communication sources (e.g., mobile phones, tablet computers, pagers, laptop computers, desk phones, message centers, white boards, patient tracking systems, or digital signage) and communication mediums (e.g., voice calls, text messages, video calls, voicemail messages, email messages, or pages) into a single manageable application. The collaboration tool may provide an interface to healthcare provider systems such as, for example, EMR systems, CPOE systems, scheduling systems, or the like.

The collaboration tool may include a command center dashboard (e.g., a user interface) that provides a single location for a healthcare provider to manage communications with other healthcare providers and with healthcare provider systems. The command center dashboard may ensure that important information (e.g., alerts, patient updates, or patient emergencies) is always displayed to the healthcare provider. The collaboration tool may include a game-like or gamification feature that provides positive reinforcement. For example, the collaboration tool may provide a set of gamification features (e.g., awards points, ribbons, badges, or prizes) for completing tasks, providing suggestions on how to use the collaboration tool, contributing to team building, or the like.

FIG. 1 is a diagram of an overview of an example implementation 100 described herein. As shown in FIG. 1, example implementation 100 may include a group of user devices 110 (e.g., a set of user devices 110-A through 110-B and a particular user device 110-C) and a healthcare provider system 120 (e.g., one or more servers storing information associated with a healthcare provider).

As further shown in FIG. 1, and by reference number 130, one of user devices 110-A through 110-B may transmit first communication information to healthcare provider system 120. First communication information may be associated with communication sources and/or communication mediums utilized by healthcare providers and/or by a user of a particular user device 110. For example, the particular user device 210 may transmit communication information that includes messages regarding patients, teleconference calls, video conference calls, hospital updates, or the like. In some implementations, first communication information may be transmitted to update a data structure of healthcare provider system 120. For example, healthcare provider system 120 may update a particular data structure that includes a calendar, a patient file, or the like based on the first communication information.

As shown by reference number 140, user device 110-C may receive the first communication information, and may receive healthcare information. Healthcare information may be associated with one or more healthcare providers. For example, user device 110-C may receive healthcare information that includes information regarding a patient, such as a patient's medical history, a treatment schedule, or the like. In some implementations, healthcare provider system 120 may transmit both the healthcare information and the first communication information to user device 110-C. Additionally, or alternatively, one of user devices 110-A through 110-B may transmit the first communication information directly to user device 110-C.

As shown by reference number 150, user device 110-C may combine the communication information and the healthcare information into a single user interface 160 and may provide user interface 160 for display. User interface 160 may provide a single location for the user to manage communications with healthcare providers and/or with healthcare provider system 120. User interface 160 may include a first section that provides information that is persistently presented within user interface 160 and may include a second section that provides positive reinforcement to the user based on utilization of user interface 160. Content of the first section may continue to be presented, in a way that remains accessible to the user, when the content of the second section changes.

In some implementations, user interface 160 may include a profile portion, an updates portion, and a patients portion. The profile portion may include a profile for a user of user device 110-C. The profile portion may include information identifying communication preferences, gamification information, or the like. The updates portion may identify a set of updates regarding actions taken, or to be taken, for a patient. The patients portion may include information identifying patients assigned to a user of user device 110-C.

In some implementations, the updates portion and the patients portion may be persistent. That is, the updates portion and the patients portion may continue to be represented within user interface 160 in a way that remains accessible to the user, even when there is a change to information displayed in the profile portion. For example, the updates portion and the patients portion may continue to be displayed such that pertinent information remains visible to a user of user interface 160 when the user provides new information via an interaction with user interface 160 or when user interface 160 receives new information for display within the profile portion. As a result, user device 110-C permits a user to maintain intelligence about patients and/or tasks represented in the updates portion and/or patients portion of user interface 160.

In some implementations, the profile portion may change to display new information. For example, user device 110-C may provide gamification information to be displayed in user interface 160. In this case, user interface 160 may display gamification information relating to one or more games associated with incentivizing a best practice, a particular user behavior (e.g., a desired behavior), or a particular action by the user. Gamification information may represent awards points, awards, badges, ribbons, prizes, or the like. In some implementations, user interface 160 may display a set of images of various badges corresponding to a set of achievements. For example, an image of a heart badge may indicate successful treatment of a cardiac patient, an image of a phone badge may indicate that the user performed 5 communication tasks, and an image of a caduceus badge may indicate that the user filled out 10 patient records.

As shown by reference number 170, user device 110-C may provide second communication information to healthcare provider system 120. For example, user device 110-C may alter user interface 160 to permit a user to communicate with another user of another user device 110 (e.g., one of user devices 110-A through 110-B). Additionally, or alternatively, user device 110-C may provide second communication information associated with updating healthcare provider system 120 regarding a status of a particular task, a location of a user of user device 110-C, or the like.

In this way, entities, such as healthcare providers, may communicate more efficiently and effectively through a combination of information within a single user interface on a user device. Additionally, or alternatively, intelligence about patients, tasks, or the like may be maintained by designating one or more portions of the user interface to provide information persistently even when one or more other portions change. Additionally, or alternatively, desirable practices of the healthcare provider may be incentivized by providing positive reinforcement within the user interface, such as gamification information that rewards achievements by the healthcare provider. Furthermore, based on centralizing communication, collaboration, patient tracking, or the like via a single user interface, an amount of time required to obtain desired information may be reduced, thereby reducing a utilization of processing resources and/or a power consumption of user device 110 relative to requiring a user to navigate multiple screens of multiple applications to obtain desired information regarding hospital activity.

As indicated above, FIG. 1 is provided merely as an example. Other example are possible and may differ from what was described with regard to FIG. 1.

Figure 2A:
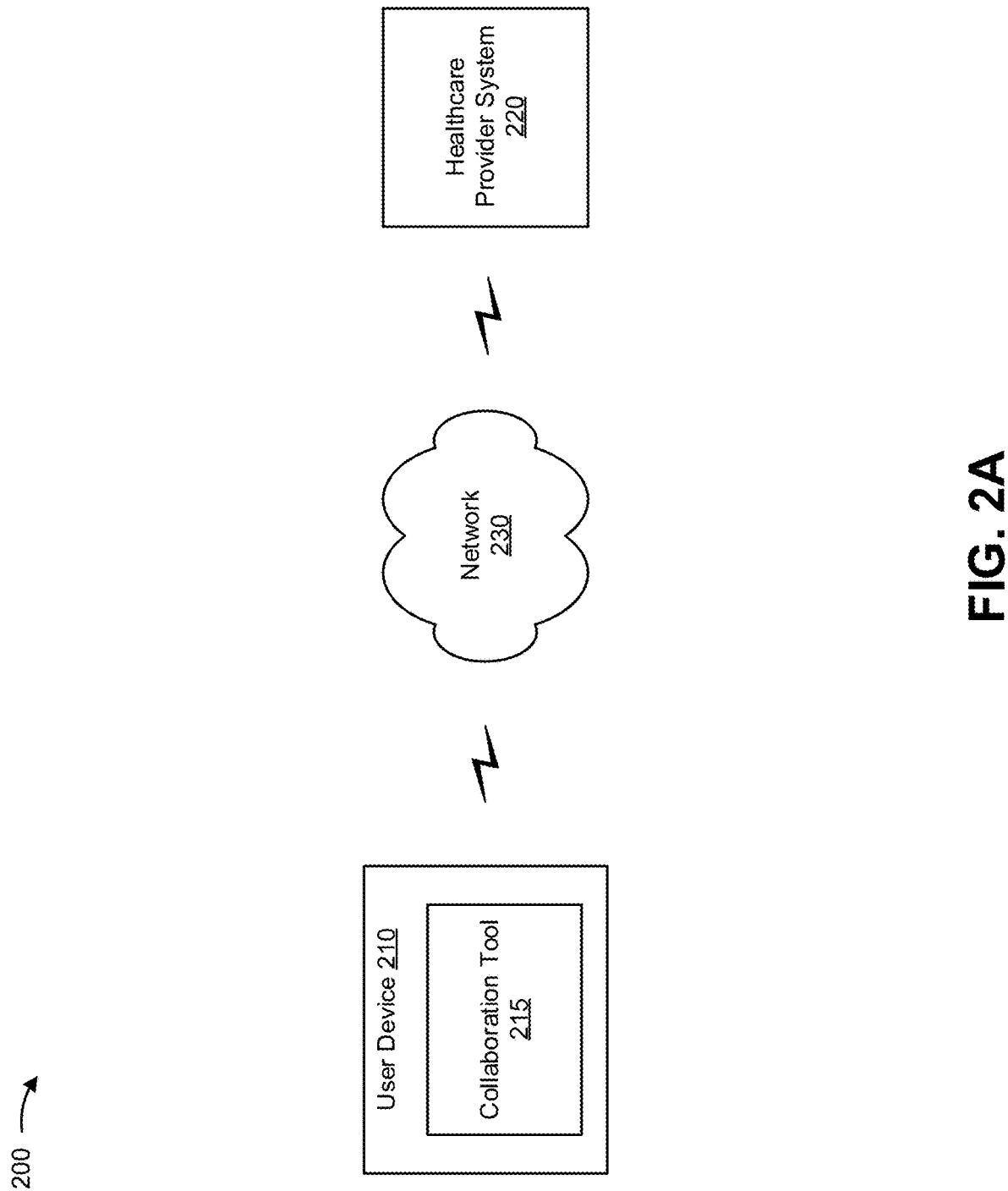
FIGS. 2A and 2B are diagrams of an example environment in which systems and/or methods, described herein, may be implemented.
Figure 2B:
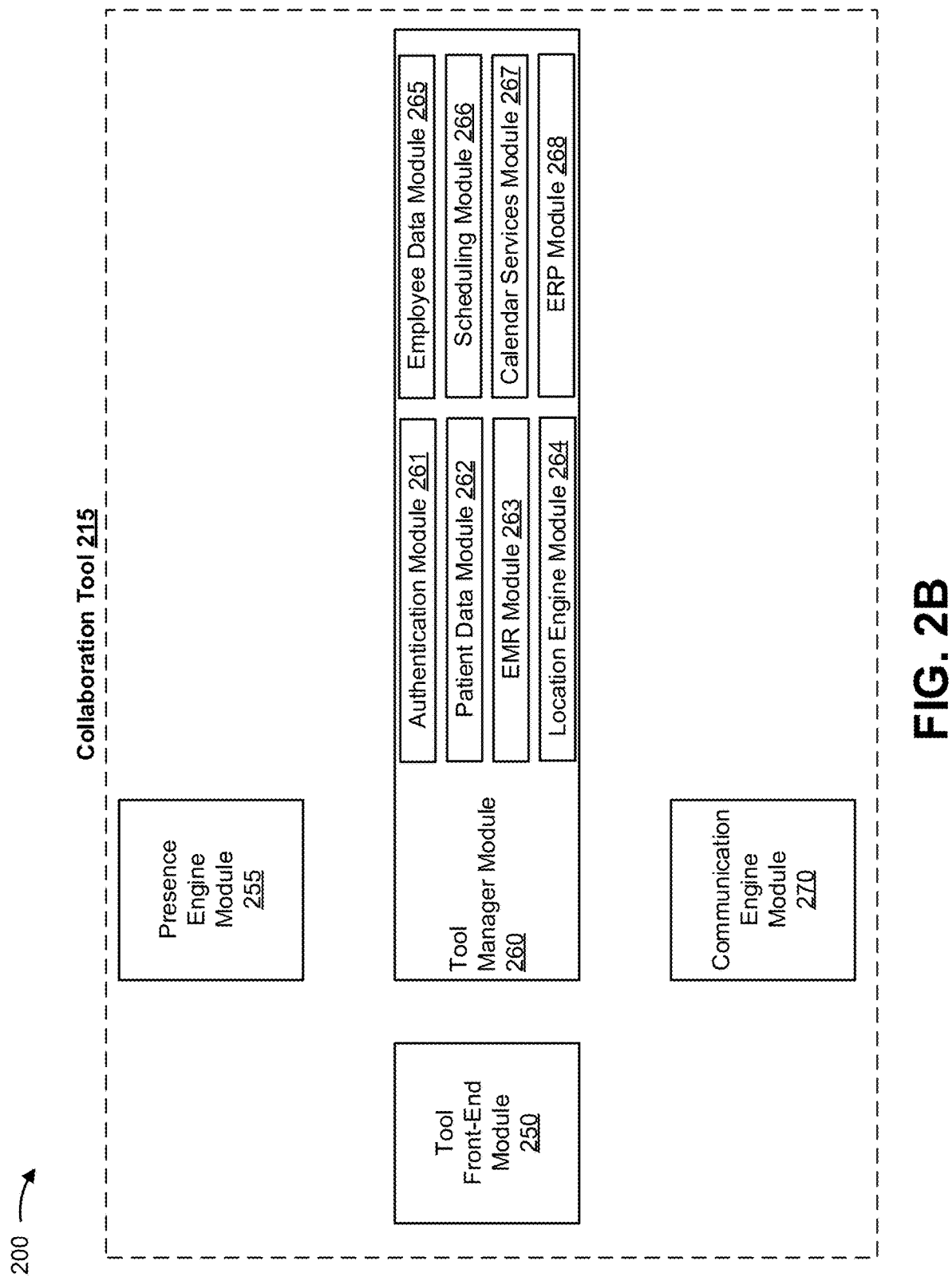

FIGS. 2A and 2B are diagrams of an example environment 200 in which systems and/or methods, described herein, may be implemented. As shown in FIG. 2A, environment 200 may include a user device 210, a collaboration tool 215, a healthcare provider system 220, and a network 230. Devices of environment 200 may interconnect via wired connections, wireless connections, or a combination of wired and wireless connections.

User device 210 includes a device capable of receiving, generating, storing, processing, and/or providing information, such as information described herein. For example, user device 210 may include a computing device, such as a desktop computer, a laptop computer, a tablet computer, a handheld computer, a smart phone, a radiotelephone, or a similar computation and communication device. In some implementations, user device 210 may communicate with healthcare provider system 220 via network 230. In some implementations, user device 210 corresponds to a user device 110 shown in FIG. 1.

Collaboration tool 215 may include an application, a code snippet, a script, a widget, or the like that causes user device 210 to perform one or more functions described herein. In some implementations, collaboration tool 215 may execute on user device 210 and a portion of collaboration tool 215 may execute on healthcare provider system 220. In some implementations, collaboration toll 215 may execute on healthcare provider system 220 and may be accessed by user device 210 (e.g., via a browser).

In some implementations, collaboration tool 215 may minimize or eliminate communication challenges associated with interruptions, patient transitions between hospital units, communication with patients and/or patient families, communication between healthcare providers, or the like. In some implementations, collaboration tool 215 may integrate multiple communication sources (e.g., mobile phones, tablet computers, pagers, laptop computers, desk phones, message centers, white boards, patient tracking systems, or digital signage) and communication mediums (e.g., voice calls, text messages, video calls, voicemail messages, email messages, faxes, or pages) into a single manageable application. In some implementations, collaboration tool 215 may provide an interface to a healthcare provider system, such as an EMR system, a CPOE system, a scheduling system, or the like.

In some implementations, collaboration tool 215 may include a command center dashboard (e.g., a user interface) that provides a single location for a healthcare provider to manage communications with other healthcare providers and with healthcare provider systems. In some implementations, the user interface (e.g., command center dashboard) may correspond to user interface 160 shown in FIG. 1. In some implementations, the command center dashboard may ensure that important information (e.g., alerts, patient updates, or patient emergencies) is always displayed to the healthcare provider. In some implementations, collaboration tool 215 may include a game-like or gamification feature that provides positive reinforcement (e.g., awards points, ribbons, badges, or prizes) for completing tasks, providing suggestions on how to use collaboration tool 215, contributing to team building, or the like. For example, collaboration tool 215 may identify a set of achievements for completion by a user, and may provide information, via user interface 160, identifying completion of one or more achievements, of the set of achievements.

In some implementations, collaboration tool 215 may cause user device 210 to receive, from healthcare provider system 220, healthcare information associated with healthcare providers, and to receive communication information associated with communication sources and communication mediums utilized by the healthcare providers and a user of user device 210. Collaboration tool 215 may cause user device 210 to combine the healthcare information and the communication information into a user interface (e.g., the command center dashboard). The command center dashboard may provide a single location for the user to manage communications with the healthcare providers and with healthcare provider system 220, may include important information that is always displayed to the user, and may include an achievement section that provides positive reinforcement to the user based on user utilization of the command center dashboard. Collaboration tool 215 may cause user device 210 to display the command center dashboard to the user.

In some implementations, collaboration tool 215 may increase processing of communications received by user device 210 (e.g., by a processor of user device 210), and may reduce processing loads on healthcare provider system 220. The reduced load on healthcare provider system 220 may reduce memory consumption and increase processing by processors of healthcare provider system 220 since the memory and processing loads may be distributed to multiple user devices 210 associated with healthcare providers.

Healthcare provider system 220 includes one or more devices capable of receiving, generating, storing, processing, and/or providing information, such as information described herein. For example, healthcare provider system 220 may include one or more computing devices, such as one or more server devices, desktop computers, workstation computers, virtual machines (VMs) provided in a cloud computing environment, or similar devices. In some implementations, healthcare provider system 220 corresponds to healthcare provider system 120 shown in FIG. 1.

In some implementations, healthcare provider system 220 may include a presence engine that provides availability information associated with healthcare providers and/or mobile devices utilized by healthcare providers; an authentication system that authenticates healthcare providers for utilization of one or more healthcare provider systems 220; a patient details system that provides information associated with patients under the care of the healthcare providers; an EMR system that provides EMRs associated with the patients; a location engine that provides physical location information associated with healthcare providers and/or mobile devices utilized by healthcare providers; a contact system that provides a directory of healthcare providers and information associated with the healthcare providers (e.g., a job description, a picture, a telephone number, or the like); a scheduling system that provides scheduling information associated with the healthcare providers (e.g., working hours, working locations, responsibilities, or the like); a calendar system that provides a calendar of events associated with the healthcare providers; an enterprise resource planning (ERP) system that integrates applications used by the healthcare providers to manage an organization (e.g., a hospital); a unified communication engine that integrates multiple communication sources and communication mediums associated with the healthcare providers; or the like. In some implementations, if healthcare provider system 220 does not include one or more of the aforementioned systems, collaboration tool 215 may provide the one or more omitted systems.

Network 230 includes one or more wired and/or wireless networks. For example, network 230 may include a cellular network, a public land mobile network (PLMN), a local area network (LAN), a personal area network (PAN) such as Bluetooth, a wide area network (WAN), a metropolitan area network (MAN), a telephone network (e.g., the Public Switched Telephone Network (PSTN)), an ad hoc network, an intranet, the Internet, a fiber optic-based network, a cloud computing network, a private network, and/or a combination of these or other types of networks.

FIG. 2B is a diagram of example components of collaboration tool 215. As shown in FIG. 2B, collaboration tool 215 may include a tool front-end module 250, a presence engine module 255, a tool manager module 260, an authentication module 261, a patient data module 262, an electronic medical record (EMR) module 263, a location engine module 264, an employee data module 265, a scheduling module 266, a calendar services module 267, an enterprise resource planning (ERP) 268, and a communication engine module 270.

Tool front-end module 250 operates one or more computing resources and is associated with providing a user interface which may correspond to user interface 160. In some implementations, tool front-end module 250 may arrange multiple portions of a user interface via a single screen to persist selected information. For example, tool front-end module 250 may arrange the updates portion and the patients portion of user interface 160 to persistently display information even when a profile portion of user interface 160 changes. In some implementations, tool front-end module 250 may receive information from tool manager module 260 to cause information to be provided via user interface 160.

Presence engine module 255 operates one or more computing resources and is associated with determining and/or providing availability information related to healthcare providers and/or mobile devices utilized by healthcare providers. For example, presence engine module 255 may determine a status of another user device 210 to determine availability of a user of the other user device 210. In some implementations, presence engine module 255 may provide a status of a user device 210 based on receiving a selection via user interface 160, based on detecting utilization of user interface 160, or the like. Additionally, or alternatively, presence engine module 255 may determine a method of communication to be utilized by a user of user device 210 based on the status determined for user device 210. In some implementations, presence engine module 255 may be associated with a presence engine interface to communicate with one or more other presence engine modules 255 or other types of presence engines.

Tool manager module 260 operates one or more computing resources and is associated with managing operation of collaboration tool 215. For example, tool manager module 260 may cause information to be provided by tool front-end module 250 for display via the user interface. Tool manager module 260 may include a group of modules (e.g., submodules), such as authentication module 261, patient data module 262, EMR module 263, location engine module 264, employee data module 265, scheduling module 266, calendar services module 267, ERP module 268, or the like.

Authentication module 261 operates one or more computing resources and is associated with authenticating healthcare providers for utilization of one or more healthcare provider systems 220. For example, authentication module 261 may perform authentication for a user based on a user name of the user, a password of the user, and/or another type of credential of the user or of user device 210. In some implementations, authentication module 261 may cause different versions of the user interface to be provided based on the authentication provided by the user. In each different version, a different set of information may be selected based on the type and identity of the user. For example, authentication module 261 may select a different version of user interface 160 for a nurse, a doctor, a patient, or a relative. In some implementations, authentication module 261 may include an authentication interface to communicate with other authentication systems. For example, authentication module 261 may utilize information that is collected by an electronic medical records (EMR) authentication system, a chat messenger authentication system, or the like.

Patient data module 262 operates one or more computing resources and is associated with providing information related to patients under the care of a healthcare provider. For example, patient data module 262 may obtain patient data such as information identifying a name, a status, a condition, a health summary, a set of medications, a set of test results, a temperature, a blood pressure, or the like. In some implementations, patient data module 262 may obtain patient data from healthcare provider system 220. In some implementations, patient data module 262 may query healthcare provider system 220. In some implementations, patient data module 262 may receive information from healthcare provider system 220 based on an update to healthcare provider system 220. Additionally, or alternatively, patient data module 262 may obtain patient data periodically. In some implementations, patient data module 262 may include a patient data interface to communicate with healthcare provider system 220.

EMR module 263 operates one or more computing resources and is associated with providing electronic medical records (EMRs) related to patients. For example, EMR module 263 may obtain EMRs from another hospital's healthcare provider system 220, an insurance provider's healthcare provider system 220, another doctor's healthcare provider system 220, or the like. In some implementations, EMR module 263 may parse an EMR to determine contents of the EMR, such as by application of a natural language processing technique. In some implementations, EMR module 263 may include an EMR interface to communicate with healthcare provider system 220. Additionally, or alternatively, EMR module 263 may provide other information, such as electronic health records (EHR), health information exchange (HIE), electronic data warehouses (EDW), and other clinical systems.

Location engine module 264 operates one or more computing resources and is associated with providing physical location information related to healthcare providers and/or related to mobile devices utilized by healthcare providers. For example, location engine module 264 may determine a location of a user device 210, of other users, or of equipment such as medical equipment, testing equipment, or the like. Additionally, or alternatively, location engine module 264 may provide wayfinding information. For example, location engine module 264 may provide the user with a route, a set of turn-by-turn directions (e.g., within a hospital or within the grounds of a hospital), or the like. In some implementations, location engine module 264 may utilize global positioning system (GPS) information to determine and provide location information. Additionally, or alternatively, location engine module 264 may communicate with a group of Bluetooth beacons inside a hospital to determine a location of user device 210 and provide directions to the user of user device 210. In some implementations, location engine module 264 may include a location interface to communicate with beacons, devices, or the like.

Employee data module 265 operates one or more computing resources and is associated with managing information related to healthcare provider employees. For example, such information may include a name, an employee identifier, a job description, a picture, a telephone number, or the like. Employee data module 265 may determine a work assignment, a work schedule, a set of tasks to be performed, a profile of a user of user device 210, a profile of other users, or the like. In some implementations, employee data module 265 may populate information identifying one or more doctors and/or one or more appointments for a patient based on employee records. In some implementations, employee data module 265 may include an employee data interface to communicate with an employee data server such as healthcare provider system 220.

Scheduling module 266 operates one or more computing resources and is associated with providing scheduling information related to healthcare providers. For example, scheduling module 266 may provide information identifying a set of working hours, working locations, responsibilities, or the like. In some implementations, scheduling module 266 may perform scheduling of patient testing, patient or employee meetings, employee shifts, or the like. In some implementations, scheduling module 266 may include a scheduling interface to communicate with a scheduling system. For example, scheduling module 266 may communicate with a local scheduling system or an online scheduling system.

Calendar services module 267 operates one or more computing resources and is associated with managing a calendar of events related to the healthcare providers. For example, calendar services module 267 may provide calendar services such as alerts, notifications of appointments, or the like, based on scheduling module 266. In some implementations, calendar services module 267 may include a calendar services interface to communicate with a calendar system, such as Outlook or Google Calendar.

ERP module 268 operates one or more computing resources and is associated with managing enterprise services related to a healthcare provider. ERP module 268 may provide and/or support an infrastructure that helps ensure supplies and other resources are available at a needed time and/or place. For example, ERP module 268 may integrate applications used by healthcare providers to manage an organization such as a hospital. In this case, ERP module 268 may provide information regarding utilization of collaboration tool 215, utilization of hospital resources, or the like. In some implementations, ERP module 268 may include an ERP interface to communicate with a separate ERP solution.

Communication engine module 270 operates one or more computing resources and is associated with integrating a set of communication sources and/or a set of communication mediums related to the healthcare providers. For example, communication sources may include mobile phones, tablet computers, pagers, laptop computers, desk phones, message centers, white boards, patient tracking systems, digital signage, or the like. Communication mediums may include voice calls, text messages, video calls, voicemail messages, email messages, pages, or the like.

The number and arrangement of devices and networks shown in FIGS. 2A and 2B are provided as an example. In practice, there may be additional devices and/or networks, fewer devices and/or networks, different devices and/or networks, or differently arranged devices and/or networks than those shown in FIGS. 2A and 2B. Furthermore, two or more devices shown in FIGS. 2A and 2B may be implemented within a single device, or a single device shown in FIGS. 2A and 2B may be implemented as multiple, distributed devices. Additionally, or alternatively, a set of devices (e.g., one or more devices) of environment 200 may perform one or more functions described as being performed by another set of devices of environment 200.

Figure 3:
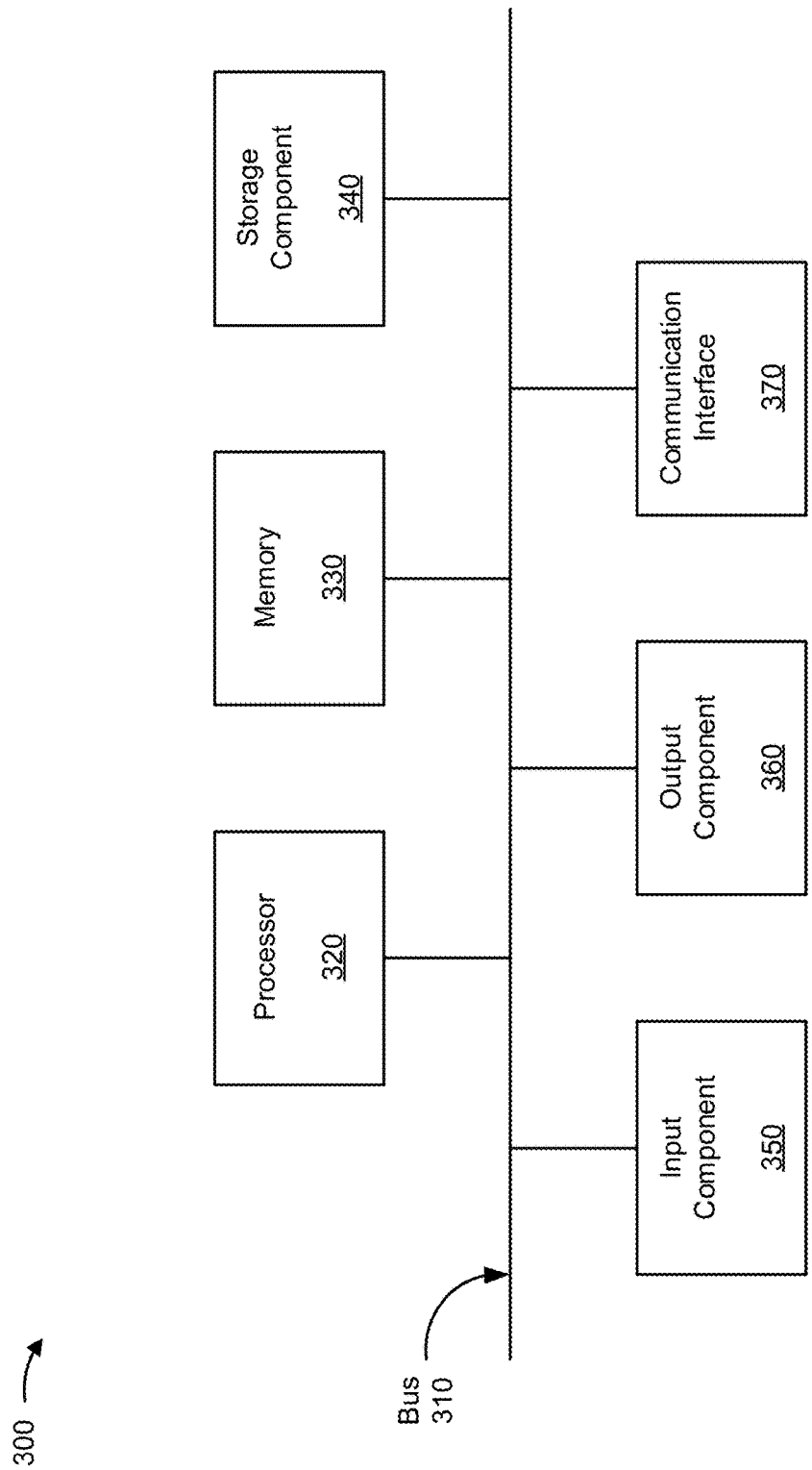
FIG. 3 is a diagram of example components of one or more devices of FIGS. 2A and 2B.

FIG. 3 is a diagram of example components of a device 300. Device 300 may correspond to user device 210, collaboration tool 215, and/or healthcare provider system 220. In some implementations, user device 210, collaboration tool 215, and/or healthcare provider system 220 may include one or more devices 300 and/or one or more components of device 300. As shown in FIG. 3, device 300 may include a bus 310, a processor 320, a memory 330, a storage component 340, an input component 350, an output component 360, and a communication interface 370.

Bus 310 includes a component that permits communication among the components of device 300. Processor 320 is implemented in hardware, firmware, or a combination of hardware and software. Processor 320 includes a processor (e.g., a central processing unit (CPU), a graphics processing unit (GPU), and/or an accelerated processing unit (APU)), a microprocessor, a microcontroller, and/or any processing component (e.g., a field-programmable gate array (FPGA) and/or an application-specific integrated circuit (ASIC)) that interprets and/or executes instructions. In some implementations, processor 320 includes one or more processors capable of being programmed to perform a function. Memory 330 includes a random access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operation and use of device 300. For example, storage component 340 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a sensor for sensing information (e.g., a GPS component, an accelerometer, a gyroscope, and/or an actuator). Output component 360 includes a component that provides output information from device 300 (e.g., a display, a speaker, and/or one or more light-emitting diodes (LEDs)).

Communication interface 370 includes a transceiver-like component (e.g., a transceiver and/or a separate receiver and transmitter) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, or the like.

Device 300 may perform one or more processes described herein. Device 300 may perform these processes in response to processor 320 executing software instructions stored by a non-transitory computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

FIG. 4 is a flow chart of an example process 400 for providing a healthcare management and communications user interface. In some implementations, one or more process blocks of FIG. 4 may be performed by collaboration tool 215. In some implementations, one or more process blocks of FIG. 4 may be performed by another device or a group of devices separate from or including collaboration tool 215, such as user device 210 and healthcare provider system 220.

As shown in FIG. 4, process 400 may include receiving healthcare information (block 410). For example, collaboration tool 215 (e.g., user device 210 and/or healthcare provider system 220) may receive healthcare information associated with a set of health care providers. In some implementations, collaboration tool 215 may receive healthcare information regarding a patient such as information identifying a condition, a health status, a set of treatments, a set of doctors, a set of nurses, a set of family members, an EMR, or the like. Additionally, or alternatively, collaboration tool 215 may receive other healthcare information such as supply chain information or an inventory of products, knowledge base information or standard of care information, instructions regarding a procedure to be performed, or the like.

In some implementations, collaboration tool 215 may receive the healthcare information from a particular healthcare provider system 220 associated with a hospital at which user device 210 is being utilized, another hospital, a medical records provider, an insurance provider, or the like. In some implementations, collaboration tool 215 may parse a document, such as by natural language processing, to obtain the healthcare information. In some implementations, collaboration tool 215 may provide, via a user interface, a questionnaire to obtain the healthcare information. For example, collaboration tool 215 may cause a medical history questionnaire to be displayed via a user interface, and may detect a user interaction with the user interface associated with indicating one or more answers to one or more questions of the medical history questionnaire. In some implementations, collaboration tool 215 may receive the healthcare information periodically. Additionally, or alternatively, collaboration tool 215 may receive the healthcare information at a time when new information is acquired by healthcare provider system 220.

As further shown in FIG. 4, process 400 may include receiving communication information (block 420). For example, collaboration tool 215 (e.g., user device 210) may receive communication information associated with one or more communication sources and/or one or more communication mediums utilized by a healthcare provider and/or by a user of user device 210. In some implementations, collaboration tool 215 may receive information regarding a patient such as a nurse or physician communication, a patient or family communication, patient transition information, or the like. Additionally, or alternatively, collaboration tool 215 may receive other communication information such as availability information. For example, collaboration tool 215 may receive information identifying a location of another user, an indication of whether the user has activated a do not disturb communication status, or the like.

Collaboration tool 215 may receive the communication information from another user device 210. For example, collaboration tool 215 may receive communication information directly from another user device 210 (e.g., via an air interface). Additionally, or alternatively, collaboration tool 215 may receive the communication information via healthcare provider system 220. In some implementations, collaboration tool 215 may receive the communication information periodically. For example, collaboration tool 215 may determine that a threshold period of time has elapsed (e.g., 1 second, 1 minute, or 1 hour), and may query healthcare provider system 220 to obtain the communication information. Additionally, or alternatively, collaboration tool 215 may receive the communication information based on information being provided by a user of another user device 210. Collaboration tool 215 may receive the communication information via a messaging system such as an instant messaging system, an email system, a teleconferencing system, a videoconferencing system, or the like. In some implementations, collaboration tool 215 may include a voice to text functionality to generate communication information regarding an audio or audio-video communication.

As further shown in FIG. 4, process 400 may include combining the healthcare information and the communication information into a user interface (block 430). For example, collaboration tool 215 (e.g., user device 210) may combine the healthcare information and the communication information into a user interface that provides a single location for the user to manage communications with a set of healthcare providers and/or a set of healthcare provider systems 220. In some implementations, the user interface may include a first section that provides information that is persistently presented in the user interface. Additionally, or alternatively, the user interface may include a second section that provides positive reinforcement to the user based on utilization of the user interface. In some implementations, the user interface may correspond to user interface 160 shown in FIG. 1.

In some implementations, collaboration tool 215 may generate a user interface which includes other information in addition to the healthcare information and the communication information, such as location information, wayfinding information, instructional information, equipment information, or the like. For example, collaboration tool 215 may generate a user interface that includes information regarding a location of equipment or medicine. Additionally, or alternatively, collaboration tool 215 may generate a user interface that includes information regarding the location of a patient. In some implementations, the user interface may include a user interface element associated with receiving a request for causing information identifying a location of an item of equipment, a medication, or a patient to be provided. For example, collaboration tool 215 may provide, via the user interface, a search box, and based on an interaction with the search box to identify a search query, location information may be provided.

In some implementations, collaboration tool 215 may generate a user interface that includes gamification information. Gamification information may include information associated with incentivizing best practices regarding patient care and/or communication. For example, collaboration tool 215 may provide gamification information identifying rewards for performing multiple tasks, prompt responses, blocking interruptions, or the like. In some implementations, collaboration tool 215 may generate gamification rewards based on clinical data. For example, collaboration tool 215 may identify a clinical practice (e.g., checking on patients regularly), and may generate a gamification reward relating to the practice, such as a badge that is displayed via the user interface when a user regularly checks on a particular patient. Additionally, or alternatively, gamification rewards may correspond to a positive outcome, such as a reduction to a rate of illness for patients of a user relative to other users, so as to automatically incentivize practices that cause a positive health outcome.

In some implementations, collaboration tool 215 may generate a reward in an area in which a user is particularly weak, such as responding to messages, so as to specifically incentivize the user to improve in that area. For example, collaboration tool 215 may track one or more statistics regarding a user of user device 210, may identify a particular statistic that satisfies a threshold, and may generate a reward associated with incentivizing improvement to the particular statistic. In this way, collaboration tool 215 improves hospital practice relative to traditional hospital communication techniques that do not include statistics tracking or gamification aspects.

In some implementations, collaboration tool 215 may generate a user interface that includes profile information. For example, collaboration tool 215 may generate a user interface that indicates communication preference information. Additionally, or alternatively, collaboration tool 215 may generate a user interface that includes contact information, such as a do not disturb status. Additionally, or alternatively, collaboration tool 215 may generate a user interface that includes location information, such as a preference regarding automatic monitoring of a location of a user of user device 210, a preference regarding availability of a user of user device 210, or the like.

In some implementations, collaboration tool 215 may classify information based on a criticality determination. For example, collaboration tool 215 may provide a severity of an alert, order a set of tasks, or the like, based on information received from healthcare provider system 220, information received from a data structure storing information regarding medical procedures and conditions, or the like. Additionally, or alternatively, collaboration tool 215 may classify healthcare actions such as a treatment action, a follow-up action, or the like. Similarly, collaboration tool 215 may classify communications, such as priority messages, urgent calls, or the like.

In some implementations, collaboration tool 215 may selectively suppress information based on availability of a user of user device 210 and a criticality of the information. For example, when the user has selected a busy status, collaboration tool 215 may classify first communication information as satisfying a threshold criticality (e.g., critical) and cause the first communication information to be provided for display via the user interface, and may classify second communication information as failing to satisfy the threshold criticality (e.g., non-critical) and suppress the second communication information from display for a threshold period of time.

In some implementations, collaboration tool 215 may designate one or more portions of the user interface as persistent portions. For example, collaboration tool 215 may cause updates, alerts, or patient lists to continue to be displayed in the user interface even when the user interface is updated to include other information, thereby preventing the hiding of critical information which could result in negative health outcomes. In some implementations, collaboration tool 215 may specify the updates portion and/or the patients portion of user interface 160 to be persistent sections that remain visible even when changes occur to the content of the profile section.

In some implementations, collaboration tool 215 may generate a user interface having a dashboard view. For example, the dashboard view may include a set of default portions. Default portions may include persistent portions, such as an updates portion and/or a patients portion. Default portions may also include user profile portions and/or gamification portions.

In some implementations, collaboration tool 215 may generate user interface elements associated with allowing communication, such as a user interface element to permit a user to compose a message, accept or reject a task, participate in a teleconference, participate in a videoconference, or the like. In some implementations, collaboration tool 215 may generate a user interface element associated with a calendar or a schedule. For example, collaboration tool 215 may generate a user interface element to permit a user to schedule a transfer, schedule a follow-up, refer a patient to a healthcare provider, or the like.

As further shown in FIG. 4, process 400 may include causing the user interface to be provided for display (block 440). For example, collaboration tool 215 (e.g., user device 210 or healthcare provider system 220) may cause the user interface to be provided for display on user device 210. In some implementations, collaboration tool 215 may monitor user utilization of the user interface to detect one or more user interactions performed by a user and update the user interface based on detecting the one or more user interactions. For example, collaboration tool 215 may provide different information via the user interface based on receiving a request for different information via an interaction with the user interface.

In some implementations, collaboration tool 215 may provide communications based on a user interaction with the user interface. For example, collaboration tool 215 may provide communications information to healthcare provider system 220, one or more other user devices 210, or the like. In some implementations, collaboration tool 215 may provide a healthcare update, such as to provide information to permit a patient transition. For example, collaboration tool 215 may provide a call to set up the transition, provide location information of a subsequent nurse for the patient to facilitate a discussion between the subsequent nurse and a user of user device 210, or the like. Additionally, or alternatively, collaboration tool 215 may provide information to permit communication with a patient's family, such as by providing alerts to update a family member after a change to a medical status, setting up a call with the family member, by automatically providing updated medical information to the family member, or the like. Additionally, or alternatively, collaboration tool 215 may provide communication between a nurse and a physician.

In some implementations, collaboration tool 215 may automatically reroute communications when user device 210 is busy. For example, when a do not disturb status has been activated, collaboration tool 215 may cause messages to be routed to another user device 210 (e.g., associated with a backup nurse, a backup doctor, or a backup therapist) for display on another user interface.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

FIGS. 5A-5I are diagrams of an example user interface 500 relating to example process 400 shown in FIG. 4. FIGS. 5A-5I show an example of collaboration tool 215 of user device 210 in various perspectives and situations. In some implementations, user interface 500 may correspond to user interface 160 shown in FIG. 1.

Figure 5A:
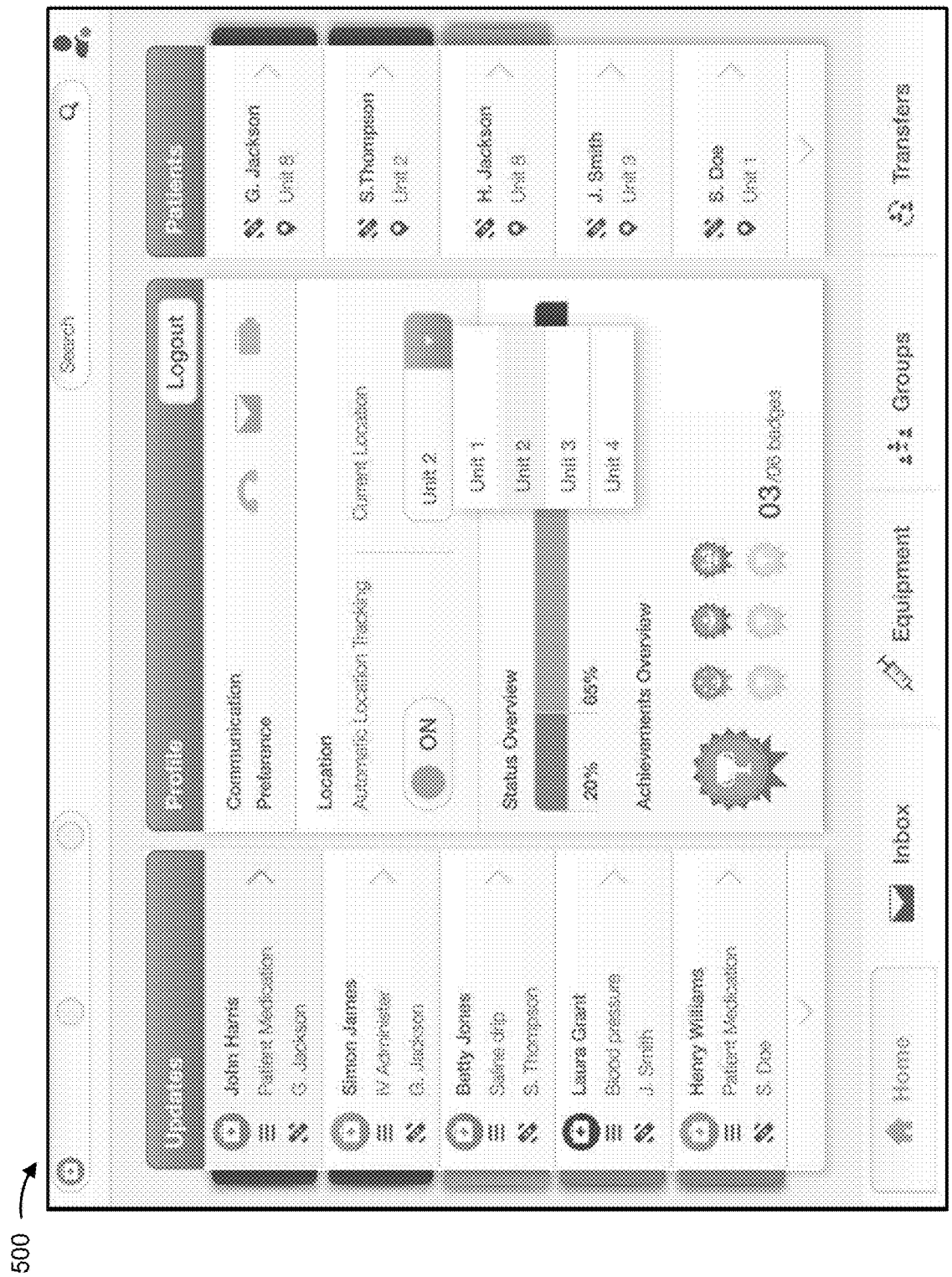
FIGS. 5A-5I are diagrams of an example implementation relating to the example process shown in FIG. 4.

As shown in FIG. 5A, collaboration tool 215 may cause user device 210 to display a command center dashboard in user interface 500. The command center dashboard may provide a single location for a healthcare provider to manage communications with other healthcare providers and with healthcare provider systems 220. In some implementations, the command center dashboard may ensure that important information (e.g., alerts, patient updates, or patient emergencies) is always displayed to the healthcare provider.

As further shown in FIG. 5A, the command center dashboard may include an updates section that provides patient updates, task updates, or the like, for the healthcare provider. In some implementations, the updates section may correspond to the updates portion of user interface 160 shown in FIG. 1.

The command center dashboard may include a profile section that provides communication preferences, location preferences, a status overview, an achievements overview, or the like, for the healthcare provider. In some implementations, the profile section may correspond to the profile portion of user interface 160 shown in FIG. 1. The achievements overview may include a game-like or gamification feature that provides positive reinforcement (e.g., a text description of an achievement, a quantity of awards points, a ribbon, a badge, or a prize) for completing tasks, providing suggestions on how to use collaboration tool 215, contributing to team building, or the like.

The command center dashboard may include a patients section that provides information identifying locations of patients associated with the healthcare provider. In some implementations, the patients section may correspond to the patients portion of user interface 160 shown in FIG. 1.

The command center dashboard may additionally provide options to view messages (e.g., an Inbox button), locate equipment or supplies (e.g., an Equipment button), locate groups of healthcare providers (e.g., a Groups button), handle patient transfers (e.g., a Transfers button), or the like.

Figure 5B:
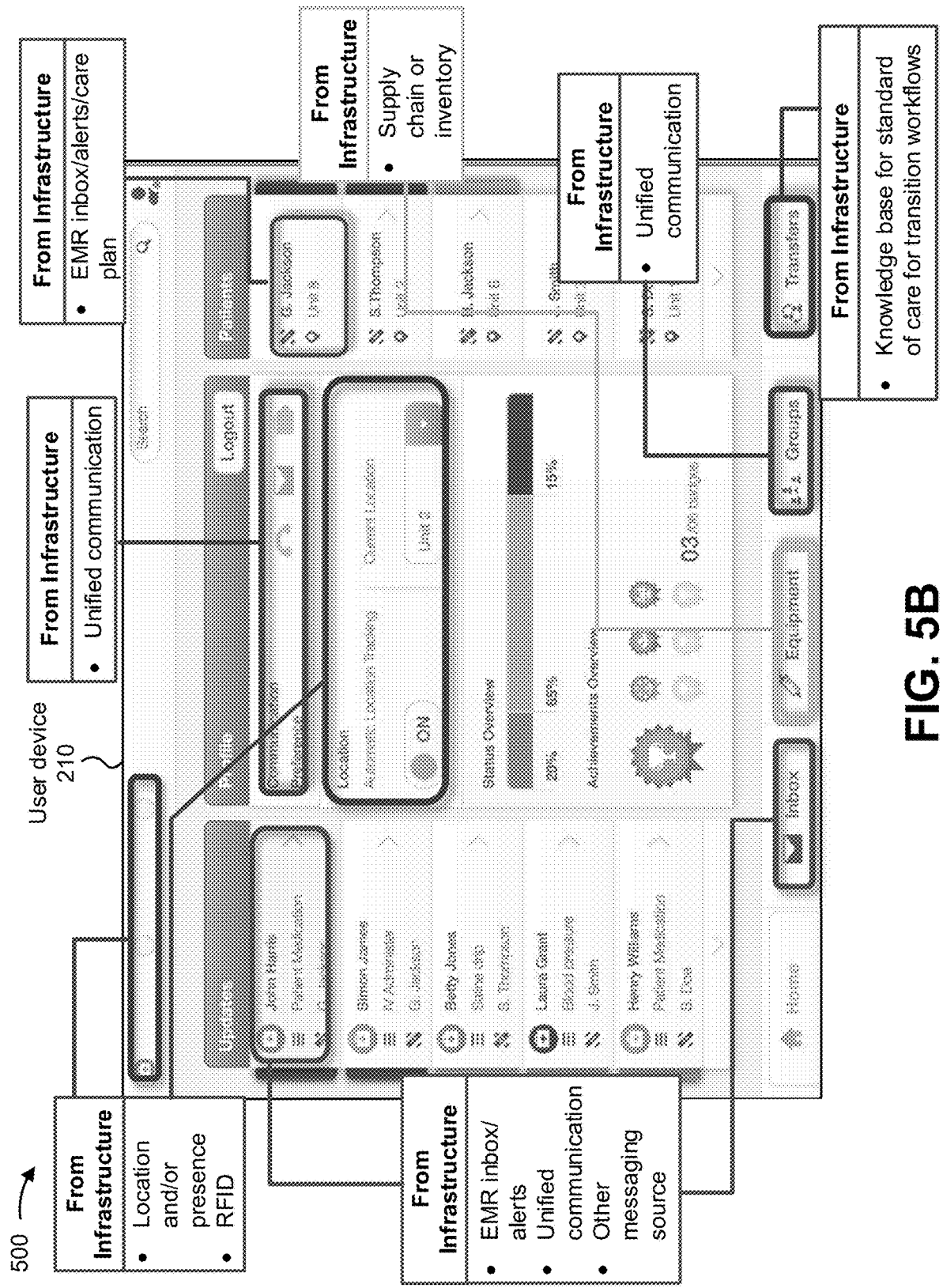

As shown in FIG. 5B, the command center dashboard may display information received from one or more healthcare provider systems 220 (referred to as infrastructure in FIG. 5B). For example, user device 210 may receive location information, presence information, radio-frequency identification (RFID) information, or the like from healthcare provider system 220, and may display the received information in the command center dashboard. User device 210 may receive EMR information, inbox messages, alerts, other messaging source information, or the like from healthcare provider system 220, and may display the received information in the updates section and the Inbox of the command center dashboard. User device 210 may receive communication preferences from a user of user device 210 and may display the communication preferences in the command center dashboard. User device 210 may receive EMR information, inbox messages, alerts, care plan information, or the like from healthcare provider system 220, and may display the received information in the patients section of the command center dashboard. User device 210 may receive supply chain information, inventory information, or the like from healthcare provider system 220, and may associate the received information with the Equipment option of the command center dashboard. User device 210 may receive group information from healthcare provider system 220, and may associate the received information with the Groups option of the command center dashboard. User device 210 may receive a knowledge base for transition workflows from healthcare provider system 220, and may associate the knowledge base with the Transitions option of the command center dashboard.

Figure 5C:

As shown in FIG. 5C, collaboration tool 215 may be securely accessed based on a healthcare provider's credentials. For example, the healthcare provider may enter credentials (e.g., user name, password, personal identification number, or biometric information), and, if the healthcare provider is authenticated based on the credentials, collaboration tool 215 may cause user device 210 to display the command center dashboard to the healthcare provider.

Figure 5D:
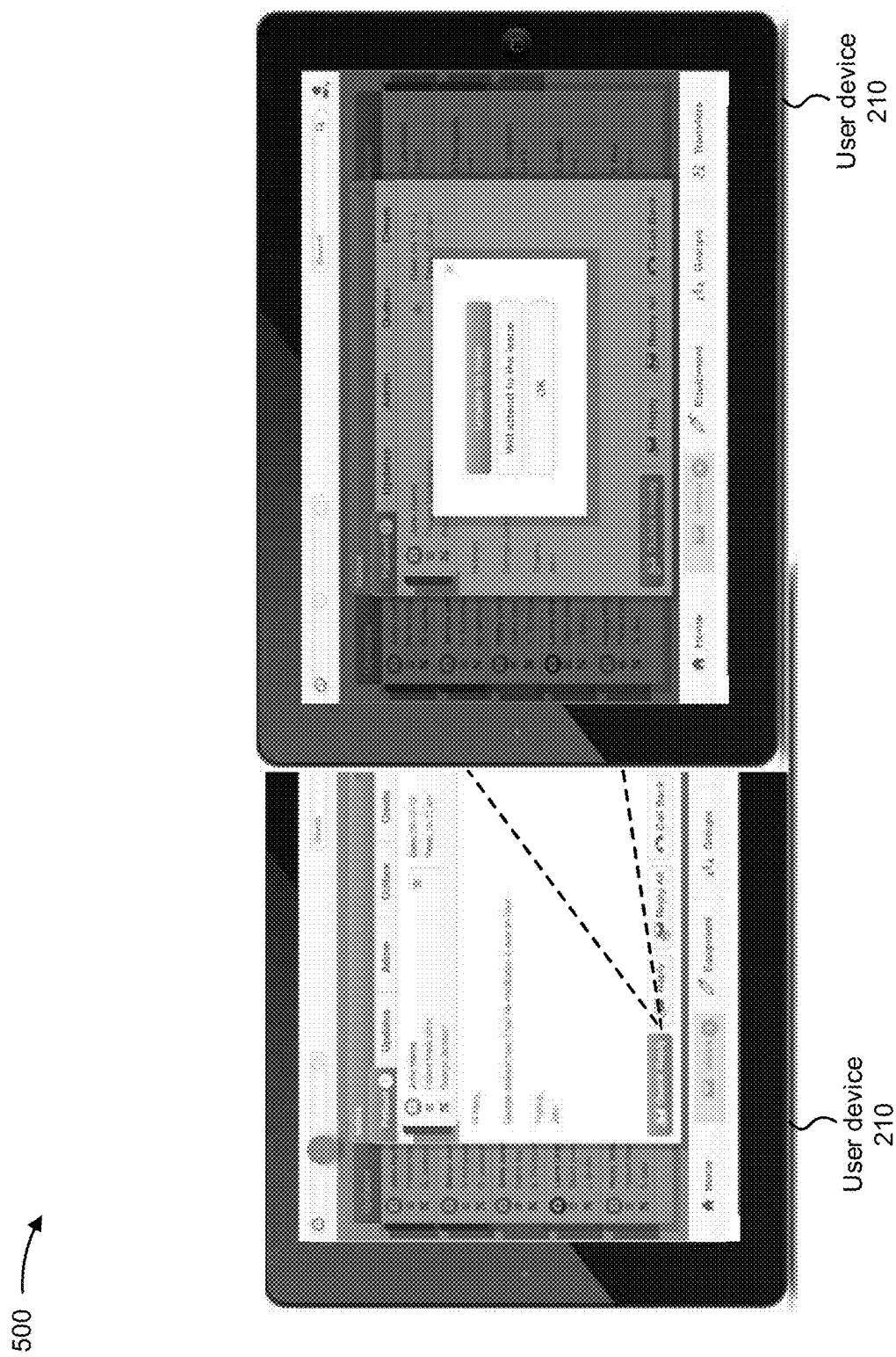

As shown in FIG. 5D, collaboration tool 215 may enable a healthcare provider to generate quick replies to messages from other healthcare providers. For example, collaboration tool 215 may enable the healthcare provider to set an availability (e.g., available, busy, not available, or the like), and may generate reply messages based on the availability. In one example, when a busy nurse cannot quickly address a message, collaboration tool 215 may generate and cause user device 210 to transmit an unable to help reply message automatically. When the nurse is unavailable, collaboration tool 215 may generate and cause user device 210 to transmit a do not disturb reply message automatically.

Figure 5E:
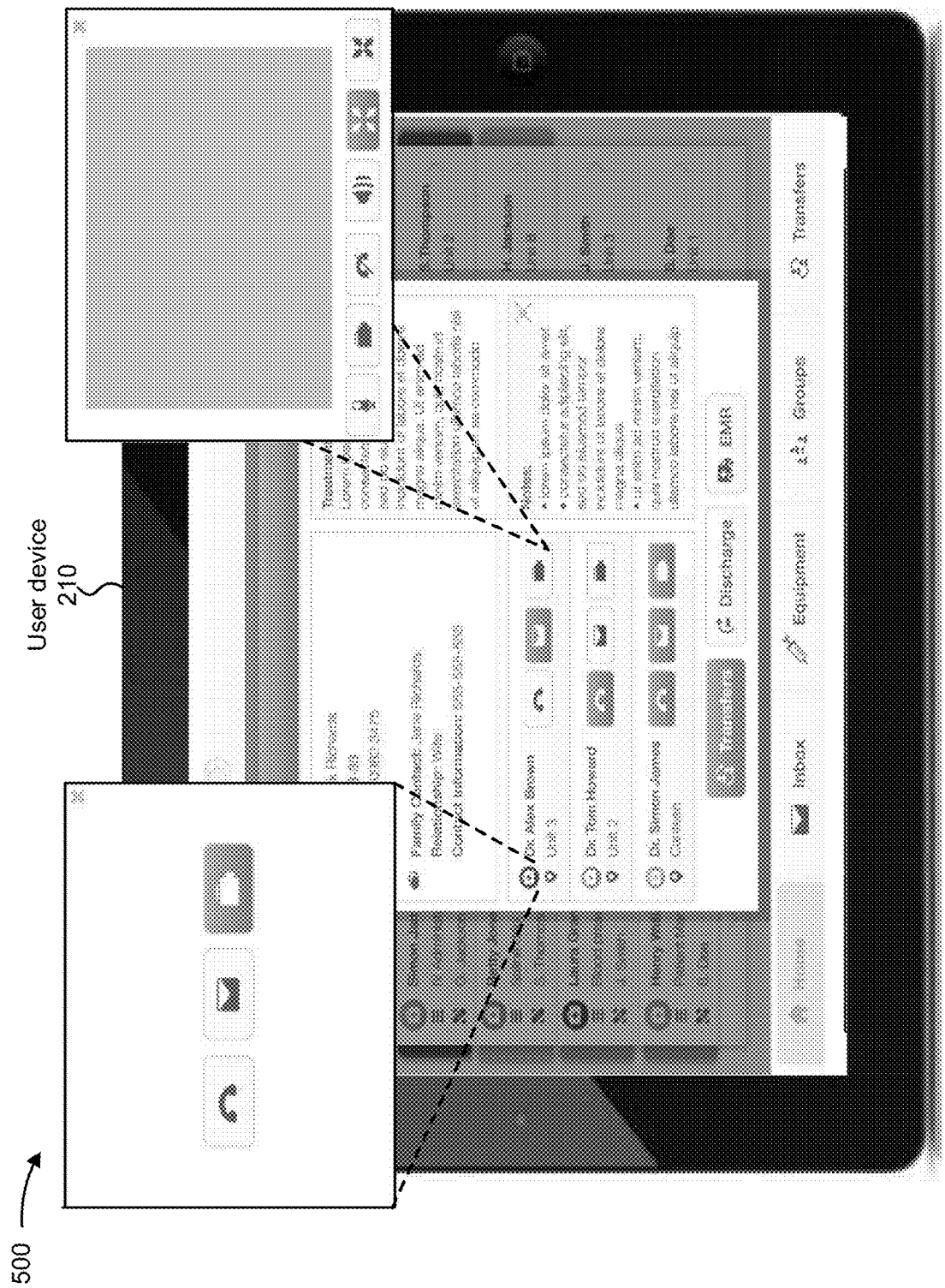

As shown in FIG. 5E, collaboration tool 215 may enable a healthcare provider to quickly and easily obtain advice and direction for patient care with virtual face-to-face communication supported with patient data. For example, as shown in FIG. 5E, collaboration tool 215 may enable a healthcare provider to conduct a video call with another healthcare provider (e.g., Dr. Alex Brown) and to view patient data while conducting the video call.

Figure 5F:
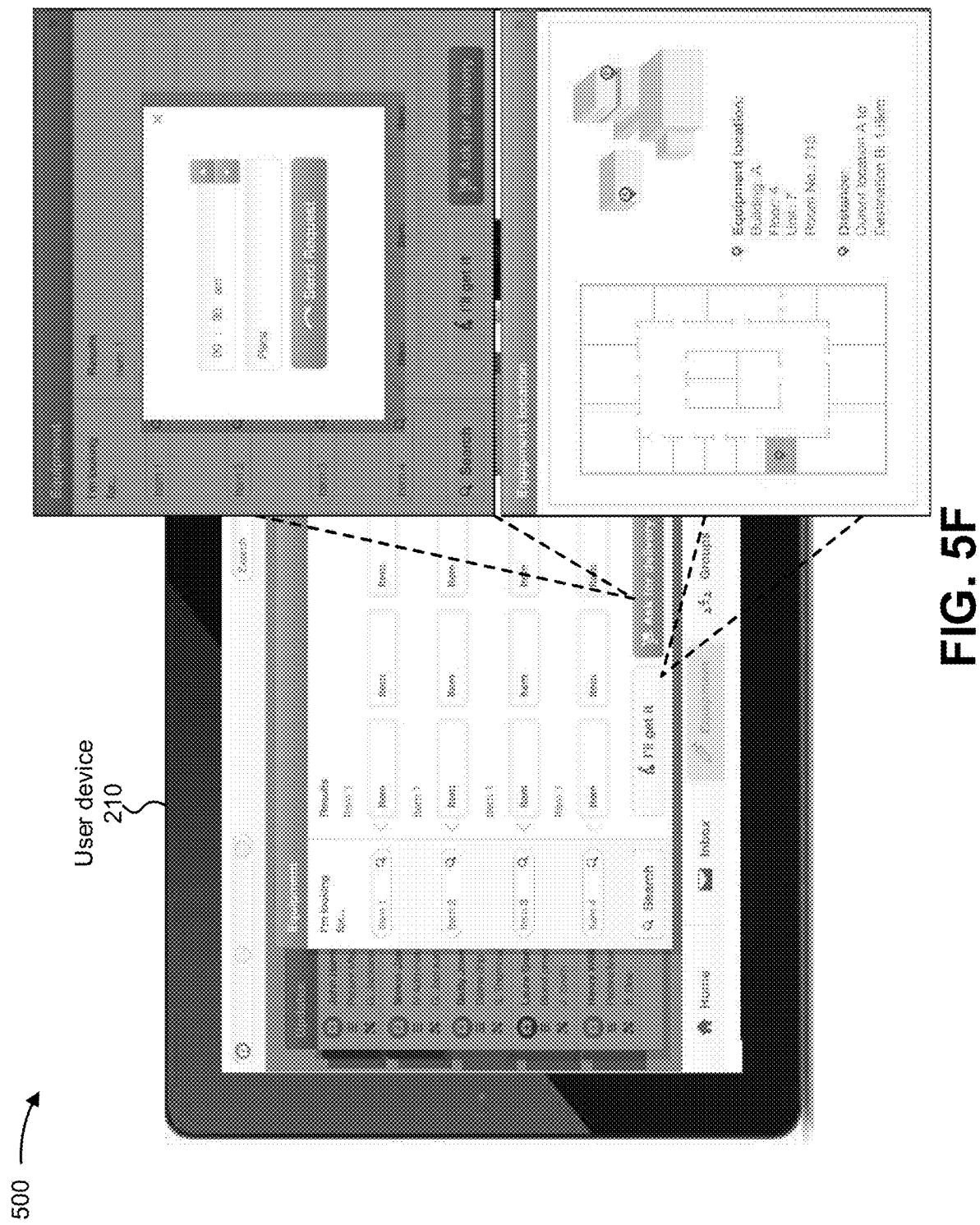

As shown in FIG. 5F, collaboration tool 215 may enable a healthcare provider to easily determine the availability of resources, such as medical equipment, medical supplies, or the like. For example, as shown in FIG. 5F, a healthcare provider may search for and request delivery of a resource, or may determine a location of the resource and physically obtain the resource.

Figure 5G:
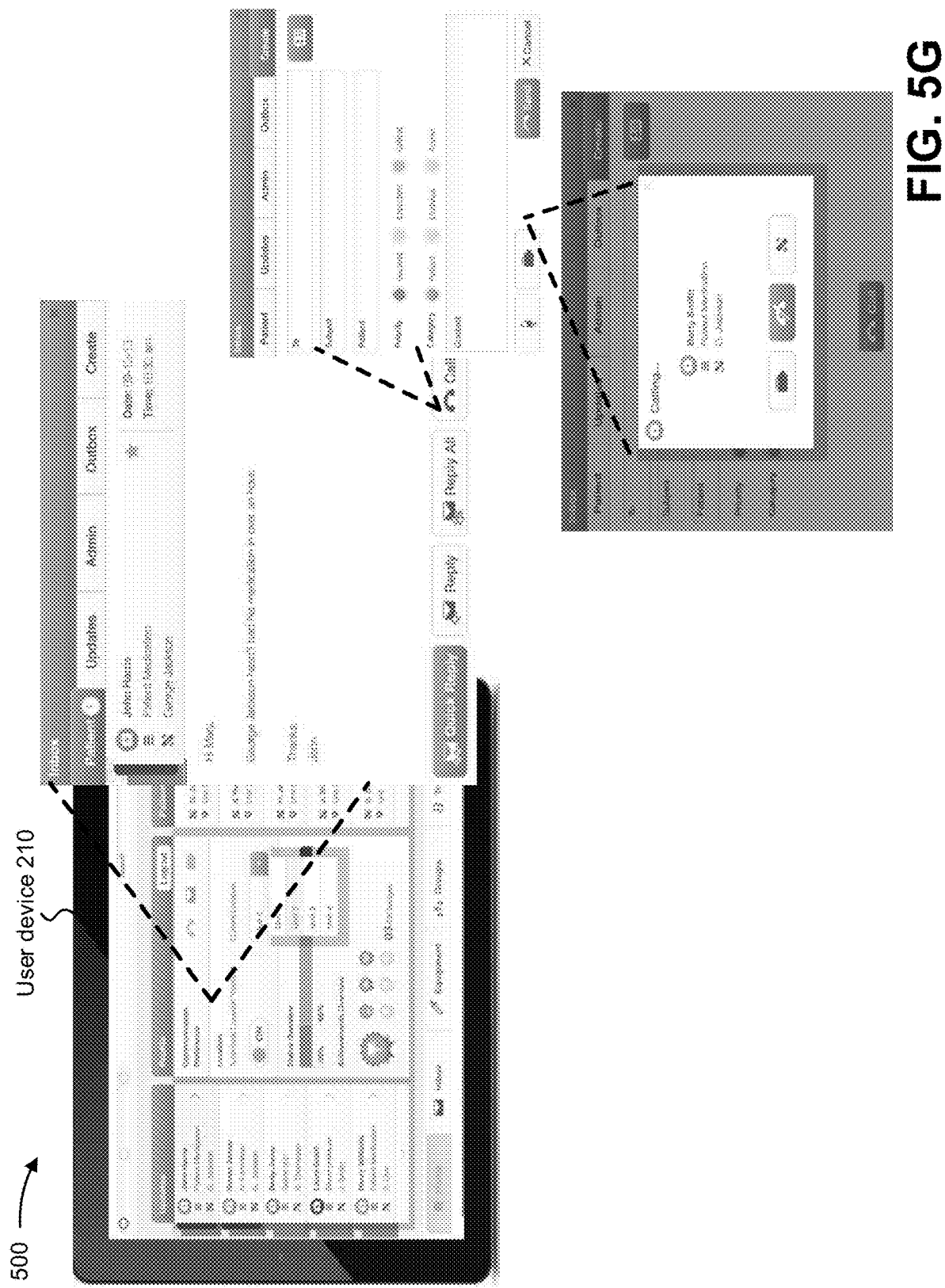

As shown in FIG. 5G, collaboration tool 215 may enable a healthcare provider to communicate and coordinate with a patient care team so that the patient's family is appropriately informed. Collaboration tool 215 may enable coordination by connecting the healthcare provider with the appropriate people in a timely and preferred manner. For example, as shown in FIG. 5G, a nurse may read a message indicating that a patient's status needs to be provided to the patient's family. While reading the message, the nurse may be interrupted from a phone call from Betty, but may choose the option to call Betty back at a later time. The nurse may return to the message, and may reply to the message by indicating that the patient is in stable condition and by asking that the patient's family be informed of this condition. The patient's family may then be updated about the patient's stable condition. Collaboration tool 215 may automatically provide an alert, at a subsequent time, regarding the option to call Betty back.

Figure 5H:

As shown in FIG. 5H, collaboration tool 215 may enable a healthcare provider to return to previous tasks after handling other more urgent tasks. For example, returning to the example of FIG. 5G and as shown in FIG. 5H, the nurse may call Betty back and may discuss where Betty will meet the nurse in order to transfer a patient. The nurse may bring the patient to an agreed-upon location, and may transfer the patient to Betty. The nurse may then utilize the Transfers option of collaboration tool 215, and may mark the patient transfer as complete.

Figure 5I:
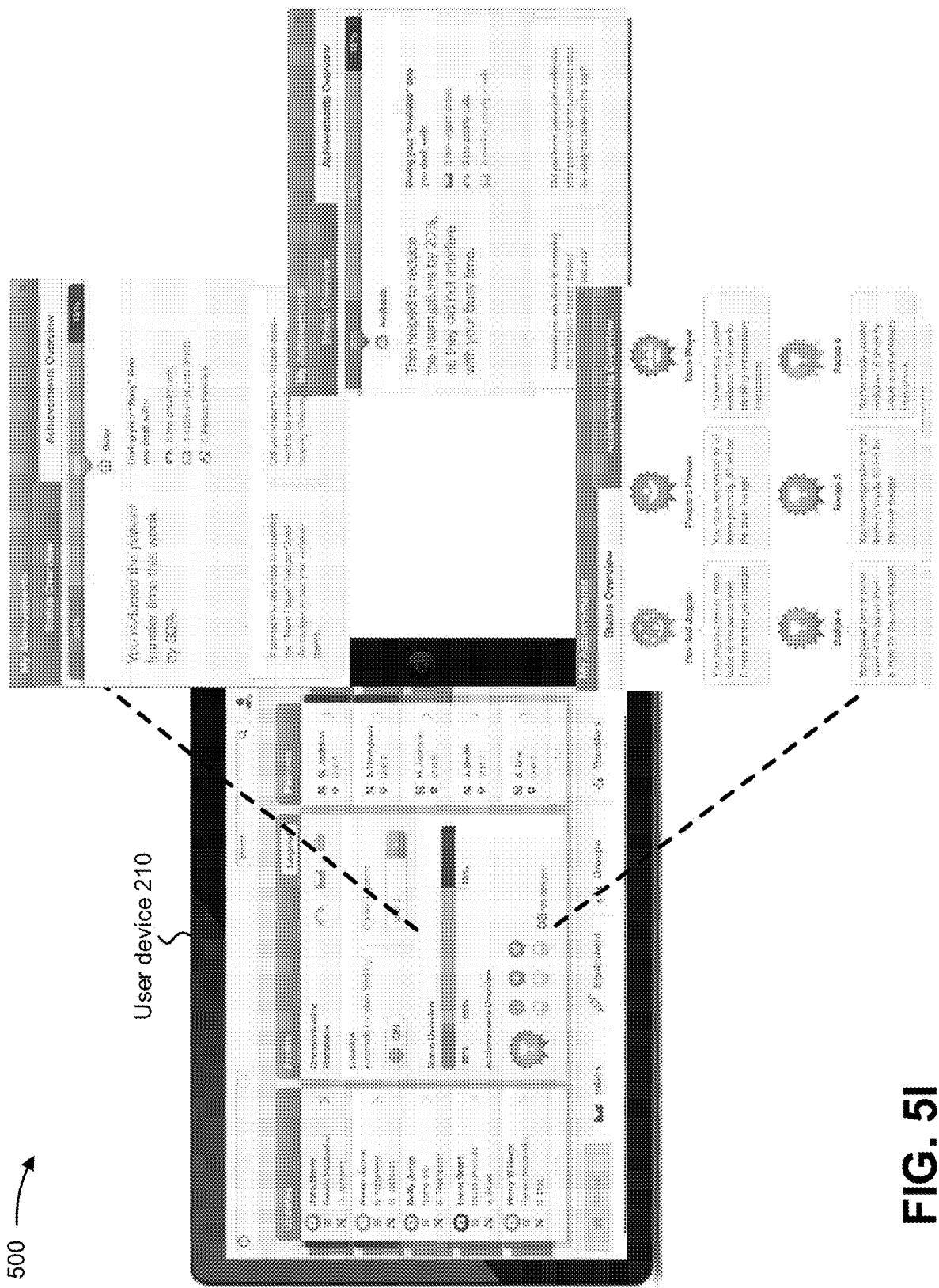

As shown in FIG. 5I, collaboration tool 215 may provide positive reinforcement to a healthcare provider via a game that provides awards as collaboration tool 215 is used, when suggestions on how to use collaboration tool 215 better are received, when a healthcare provider contributes to team building, or the like. For example, as shown in FIG. 5I, a nurse may review awards or achievements received during the day, such as points earned for setting a status appropriately, reducing patient transfer time, reducing interruptions, or the like.

As indicated above, FIGS. 5A-5I are provided merely as an example. Other examples are possible and may differ from what was described with regard to FIGS. 5A-5I. In some implementations, the various operations described in connection with FIGS. 5A-5I may be performed automatically or at the request of a user.

In this way, user device 210 permits for centralized communication, collaboration, and patient tracking in a single user interface. As a result, user device 210 permits healthcare providers to communicate with each other and with patient family members more efficiently and effectively, reducing distractions and providing improved patient outcomes. Moreover, user device 210 may permit information to be obtained more quickly and processing loads, memory use, and energy consumption may be reduced relative to requiring a user to navigate multiple screens of multiple applications to obtain desired information.

Additionally, or alternatively, implementations described herein may provide a user interface that persistently displays designated information, such as update information and patient information, even when there are changes to other information, such as profile information, in the user interface.

Additionally, or alternatively, implementations described herein may provide a user interface that generates positive reinforcement information, such as gamification information, to reward achievements by a healthcare provider. As a result, practices of the healthcare provider that generate better patient outcomes may be incentivized.

The foregoing disclosure provides illustration and description, but is not intended to be exhaustive or to limit the implementations to the precise form disclosed. Modifications and variations are possible in light of the above disclosure or may be acquired from practice of the implementations.

As used herein, the term component is intended to be broadly construed as hardware, firmware, and/or a combination of hardware and software.

Some implementations are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, etc.

Certain user interfaces have been described herein and/or shown in the figures. A user interface may include a graphical user interface, a non-graphical user interface, a text-based user interface, etc. A user interface may provide information for display. In some implementations, a user may interact with the information, such as by providing input via an input component of a device that provides the user interface for display. In some implementations, a user interface may be configurable by a device and/or a user (e.g., a user may change the size of the user interface, information provided via the user interface, a position of information provided via the user interface, etc.). Additionally, or alternatively, a user interface may be pre-configured to a standard configuration, a specific configuration based on a type of device on which the user interface is displayed, and/or a set of configurations based on capabilities and/or specifications associated with a device on which the user interface is displayed.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A collaboration device, comprising:
   a memory;
   a network interface communicatively coupled to one or more beacons; and
   one or more processors to:
      communicate with a first device to receive first data,
         the first data being associated with a set of entities;
      communicate with a second device to receive second data,
         the second data being associated with a set of communication sources and a set of communication mediums utilized by the set of entities and a user of the collaboration device;
      combine the first data and the second data into a user interface,
         the user interface providing a single location for displaying communications with the set of entities and with a system associated with the set of entities,
         the user interface including a first section that provides information that is persistently presented in the user interface,
         the user interface including a second section that provides information that is selectively presented in the user interface;
      provide the user interface for display;
      determine, from the network interface, a location of the collaboration device;
      determine, from the network interface, a location of the first device or the second device;
      generate directions from the collaboration device to the first device or the second device based on the location of the collaboration device and the location of the first device or the second device;
      determine a communication status associated with the second device,
         the communication status indicating an availability of a user of the second device;
      provide, in the user interface, the communication status associated with the second device; and
      determine a method of communication for the user of the collaboration device based on the communication status associated with the second device.

2. The collaboration device of claim 1, where the one or more processors, when combining the first data and the second data into the user interface, are to:
   provide, via the second section of the user interface, a set of gamification features associated with providing positive reinforcement to the user based on utilization of the user interface for communication.

3. The collaboration device of claim 1, where the first device is associated with a healthcare provider system; and where the one or more processors, when communicating with the first device to receive first data, are to:
   communicate with the first device to receive healthcare information associated with a set of healthcare providers.

4. The collaboration device of claim 1, where the second device is a user device; where the one or more processors, when communicating with the second device to receive the second data, are to:
   communicate with the second device to receive the second data relating to at least one of:
      a voice call, a video call,
a fax,
an instant message,
a page,
a text message, or
an email; and
where the one or more processors, when determining the communication status associated with the second device, are to:
determine the communication status based on detecting utilization of a user interface of the second device.

5. The collaboration device of claim 1, where the one or more processors, when combining the first data and the second data into the user interface, are to:
provide, via the second section of the user interface, wayfinding information associated with directing the user of the collaboration device to a location associated with the set of entities.

6. The collaboration device of claim 1, where the one or more processors, when combining the first data and the second data into the user interface, are to:
persistently provide, via the first section of the user interface, information identifying a set of patients of a healthcare provider that are assigned to the user of the collaboration device; and
persistently provide, via the first section of the user interface, information identifying a set of tasks that are to be performed by the user of the collaboration device, one or more tasks, of the set of tasks, relating to a patient of the set of patients.

7. The collaboration device of claim 1, where the one or more processors are further to:
detect a user interaction with the user interface associated with indicating that the collaboration device is to suppress one or more messages;
receive a particular message after detecting the user interaction;
classify the particular message based on a measure of criticality of the particular message; and
selectively suppress the particular message based on the measure of criticality and the user interaction with the user interface associated with indicating that the collaboration device is to suppress one or more messages.

8. The collaboration device of claim 7, where the one or more processors, when classifying the particular message based on the measure of criticality, are to:
classify the particular message as satisfying a threshold criticality; and
where the one or more processors, when selectively suppressing the particular message, are to:
provide the particular message via the user interface based on classifying the particular message as satisfying the threshold criticality.

9. The collaboration device of claim 7, where the one or more processors, when classifying the particular message based on the measure of criticality, are to:
classify the particular message as failing to satisfy a threshold criticality; and
where the one or more processors, when selectively suppressing the particular message, are to:
omit the particular message from display via the user interface based on classifying the particular message as failing to satisfy the threshold criticality; and
transmit the particular message to a communication device associated with another user based on omitting the particular message from display via the user interface.

10. The collaboration device of claim 7, where the one or more processors, when classifying the particular message based on the measure of criticality, are to:
classify the particular message as failing to satisfy a threshold criticality; and
where the one or more processors, when selectively suppressing the particular message, are to:
omit the particular message from display via the user interface based on classifying the particular message as failing to satisfy the threshold criticality;
determine, after omitting the particular message from display, that a threshold period of time has elapsed from receiving the particular message; and
provide, via the user interface, information identifying the particular message based on determining that the threshold period of time has elapsed from receiving the particular message.

11. A non-transitory computer-readable medium storing instructions, the instructions comprising:
one or more instructions that, when executed by one or more processors of a collaboration device, the collaboration device comprising a network interface communicatively coupled to one or more beacons, cause the one or more processors to:
receive, from a healthcare provider system, healthcare information associated with a set of healthcare providers;
receive communication information associated with the set of healthcare providers and a user of the collaboration device;
combine the healthcare information and the communication information into a user interface,
the user interface including a first section that provides information that is persistently presented in the user interface and relates to a set of alerts or a set of tasks associated with a set of patients of the set of healthcare providers and the user,
the user interface including a second section that selectively provides positive reinforcement to the user based on utilization of the user interface;
provide the user interface for display;
update the second section of the user interface based detecting utilization of the user interface by the user;
determine, from the network interface, a location of the collaboration device;
determine, from the network interface, a location of the healthcare provider system;
generate directions from the collaboration device to the healthcare provider system based on the location of the collaboration device and the location of the healthcare provider system;
determine a communication status associated with a communication device,
the communication status indicating an availability of a health care provider, of the set of health care providers, associated with the communication device;
provide, in the user interface, the communication status associated with the communication device; and
determine a method of communication for the user of the collaboration device based on the communication status associated with the communication device.

12. The non-transitory computer-readable medium of claim 11, where the one or more instructions, when executed by the one or more processors, further cause the one or more processors to:

update the second section of the user interface to provide information associated with a user profile of the user, the user interface including a set of user interface elements associated with receiving input to alter a set of preferences relating to the user.

13. The non-transitory computer-readable medium of claim 11, where the one or more instructions, when executed by the one or more processors, further cause the one or more processors to:
receive input, via the user interface, associated with requesting location information relating to an entity within a hospital,
the entity including at least one of another healthcare provider, of the set of healthcare providers, an item of equipment, or a medication;
determine a location of the entity; and
update the second section of the user interface to provide information identifying the location of the entity within the hospital.

14. The non-transitory computer-readable medium of claim 11, where the one or more instructions, that cause the one or more processors to update the second section of the user interface, are further to:
update the second section of the user interface to provide information identifying an achievement of the user,
the second section of the user interface being caused to include at least one of:
a text description of the achievement,
a badge relating to the achievement,
information identifying a quantity of awards points awarded for the achievement,
a ribbon relating to the achievement, or
information identifying a prize awarded for the achievement.

15. The non-transitory computer-readable medium of claim 11, where the one or more instructions, when executed by the one or more processors, cause the one or more processors to:
identify, based on the healthcare information, a set of achievements for completion by the user,
the set of achievements relating to utilization of the user interface to respond to the set of alerts or complete the set of tasks;
monitor user utilization of the user interface;
determine, based on monitoring user utilization of the user interface, that the user has satisfied a set of requirements relating to a particular achievement of the set of achievements; and
where the one or more instructions, that cause the one or more processors to update the second section of the user interface, are to:
update the second section of the user interface to provide an indication that the user has satisfied the set of requirements relating to the particular achievement.

16. The non-transitory computer-readable medium of claim 11, where the one or more instructions, that cause the one or more processors to combine the healthcare information and the communication information into the user interface, are to:
provide a user interface element associated with identifying a communication with a particular healthcare provider of the set of healthcare providers;
receive input to the collaboration device associated with a response to the communication; and
transmit, to another device associated with the particular healthcare provider, information identifying the response to the communication.

17. A method, comprising:
receiving, by one or more first devices and from a plurality of healthcare provider systems, healthcare information associated with a plurality of healthcare providers;
receiving, by the one or more first devices, communication information associated with a plurality of communication sources and a plurality of communication mediums utilized by the plurality of healthcare providers and a user of a user device;
combining, by the one or more first devices, the healthcare information and the communication information into a user interface,
the user interface providing a single location for the user to manage communications with the plurality of healthcare providers and with the plurality of healthcare provider systems,
the user interface including a first section that provides information that is persistently presented in the user interface,
the user interface including a second section that provides positive reinforcement to the user based on utilization of the user interface;
providing, by the one or more first devices, the user interface for display;
determining, by the one or more first devices and from one or more network interfaces of the one or more first devices, communicatively coupled to one or more beacons, a location of the user device;
determining, by the one or more first devices and from the one or more network interfaces of the one or more first devices, a location of a healthcare provider system of the plurality of healthcare provider systems;
generating, by the one or more first devices, directions from the user device to the healthcare provider system based on the location of the user device and the location of the healthcare provider system;
determining, by the one or more first devices, a communication status associated with a second device,
the communication status indicating an availability of a healthcare provider, of the plurality of healthcare providers, associated with the second device, and
the second device being associated with the plurality of communication mediums;
providing, by the one or more first devices and in the user interface, the communication status; and
determining, by the one or more first devices, a method of communication for the user of the user device based on the communication status associated with the second device.

18. The method of claim 17, further comprising:
monitoring the location of the user device; and
periodically providing information identifying the location of the user device.

19. The method of claim 17, where receiving the communication information comprises:
receiving an alert; and
where providing the user interface for display comprises:
providing, for display via the second section of the user interface, the alert.

20. The method of claim 17, further comprising:
monitoring user utilization of the user interface to identify a user behavior that fails to comply with a desired behavior, the desired behavior being associated with user utilization of the user interface;

generate an achievement for completion by the user associated with causing the user to comply with the desired behavior; and provide, via the second section of the user interface, information identifying the achievement to provide positive reinforcement to the user.

\* \* \* \* \*